(12) United States Patent
Garcia Coni

(10) Patent No.: US 9,730,763 B2
(45) Date of Patent: Aug. 15, 2017

(54) HEAD RESTRAINING APPARATUS FOR A MEDICAL PROCEDURE

(71) Applicant: Mariana Garcia Coni, Toronto (CA)

(72) Inventor: Mariana Garcia Coni, Toronto (CA)

(73) Assignee: SYNAPTIVE MEDICAL (BARBADOS) INC., Bridgetown (BB)

( * ) Notice: Subject to any disclaimer, the term of this patent is extended or adjusted under 35 U.S.C. 154(b) by 0 days.

(21) Appl. No.: 14/906,448

(22) PCT Filed: Oct. 17, 2014

(86) PCT No.: PCT/CA2014/051003
§ 371 (c)(1),
(2) Date: Jan. 20, 2016

(87) PCT Pub. No.: WO2016/058077
PCT Pub. Date: Apr. 21, 2016

(65) Prior Publication Data
US 2016/0317243 A1    Nov. 3, 2016

(51) Int. Cl.
*A61B 90/18*    (2016.01)
*A61G 13/12*    (2006.01)
(Continued)

(52) U.S. Cl.
CPC ............ *A61B 90/18* (2016.02); *A61G 7/072* (2013.01); *A61G 13/121* (2013.01);
(Continued)

(58) Field of Classification Search
CPC .... A61F 5/3776; A61F 5/3715; A61F 5/3723; A61F 5/055; E05B 75/00; A61G 13/12;
(Continued)

(56) References Cited

U.S. PATENT DOCUMENTS

| 4,256,112 A | 3/1981 | Kopf et al. |
| 4,400,820 A | 8/1983 | O'Dell et al. |

(Continued)

FOREIGN PATENT DOCUMENTS

EP    2425781 A1    7/2012

OTHER PUBLICATIONS

Gullmar et al., "Evaluation of a MR Compatible Head Fixation Device Using a Custom-Made 3D Printed Frame in Combination with a Thermoplastic Head Mask", Proceedings of International Society Magnetic Resonance, Issue 22, 2014.
(Continued)

*Primary Examiner* — Ophelia A Hawthorne
(74) *Attorney, Agent, or Firm* — Ridout & Maybee LLP

(57) ABSTRACT

A head restraining device is provided for securing a patient's head to a bed. The head restraining device has a frame, a lower compliant support strap, and an upper compliant support strap. The frame has a first anchor assembly, a second anchor assembly, and a connecting mechanism for connecting the frame to the bed. The compliant support straps have a first end and a second end and support a portion of the patient's head. The first end of the upper compliant support strap and the first end of the lower compliant support strap are securable by the first anchor assembly and the second end of the upper compliant support strap and the second end of the lower compliant support strap are securable by the second anchor assembly. The head restraining device may be used for any surgical procedure where head fixation is needed.

13 Claims, 17 Drawing Sheets

(51) Int. Cl.
*A61G 7/07* (2006.01)
*A61B 34/20* (2016.01)
*A61B 90/10* (2016.01)

(52) U.S. Cl.
CPC .. *A61G 13/1265* (2013.01); *A61B 2034/2055* (2016.02); *A61B 2090/103* (2016.02); *A61G 7/07* (2013.01)

(58) Field of Classification Search
CPC .............. A61G 13/121; A61G 13/1235; A61G 13/1245; A61G 7/072; A61G 13/1265; A47C 15/008; A61B 90/18; A61B 2034/2055; A61B 2090/103
See application file for complete search history.

(56) References Cited

U.S. PATENT DOCUMENTS

| | | | |
|---|---|---|---|
| 5,337,760 A | 8/1994 | Nichols | |
| 5,388,580 A | 2/1995 | Sullivan et al. | |
| 5,702,406 A * | 12/1997 | Vilsmeier | A61B 90/14 128/845 |
| 8,099,150 B2 | 1/2012 | Piferi et al. | |
| 8,292,505 B2 | 10/2012 | Tybinkowski et al. | |
| 8,734,372 B1 | 5/2014 | Graham | |
| 2005/0160532 A1* | 7/2005 | Froelich | A61G 13/12 5/637 |
| 2010/0276056 A1* | 11/2010 | Traboulsi | B32B 7/12 156/60 |
| 2013/0331688 A1 | 12/2013 | Heigl et al. | |
| 2014/0024925 A1 | 1/2014 | Piferi | |
| 2014/0076331 A1 | 3/2014 | Cho et al. | |

OTHER PUBLICATIONS

Canadian Intellectual Property Office, International Search Report and Written Opinion dated Jun. 2, 2015 in respect of PCT Application No. PCT/CA2014/051003.

* cited by examiner

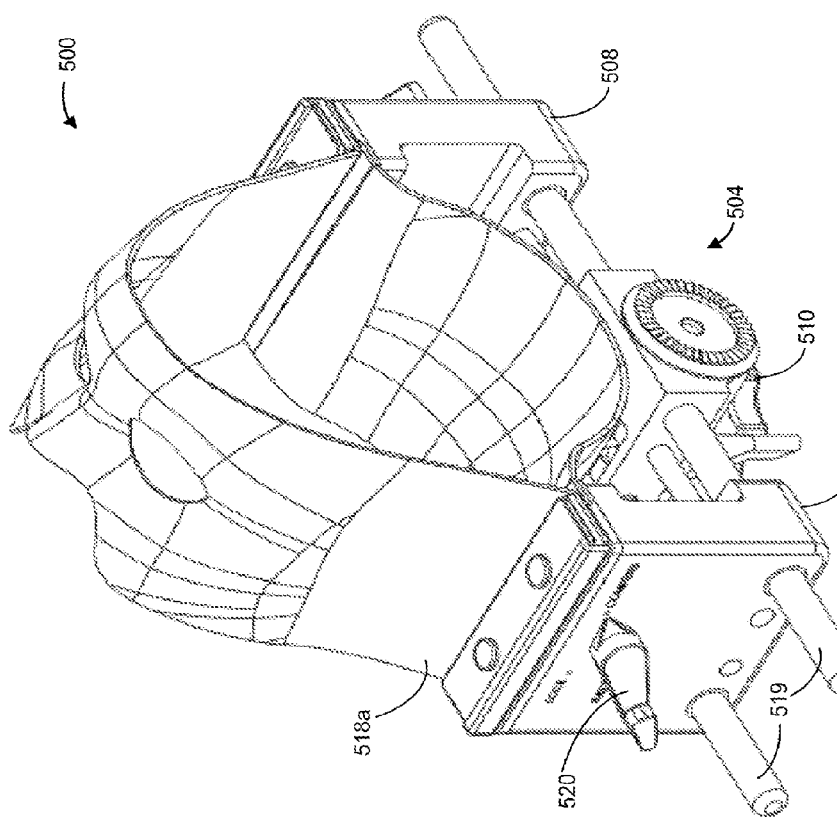

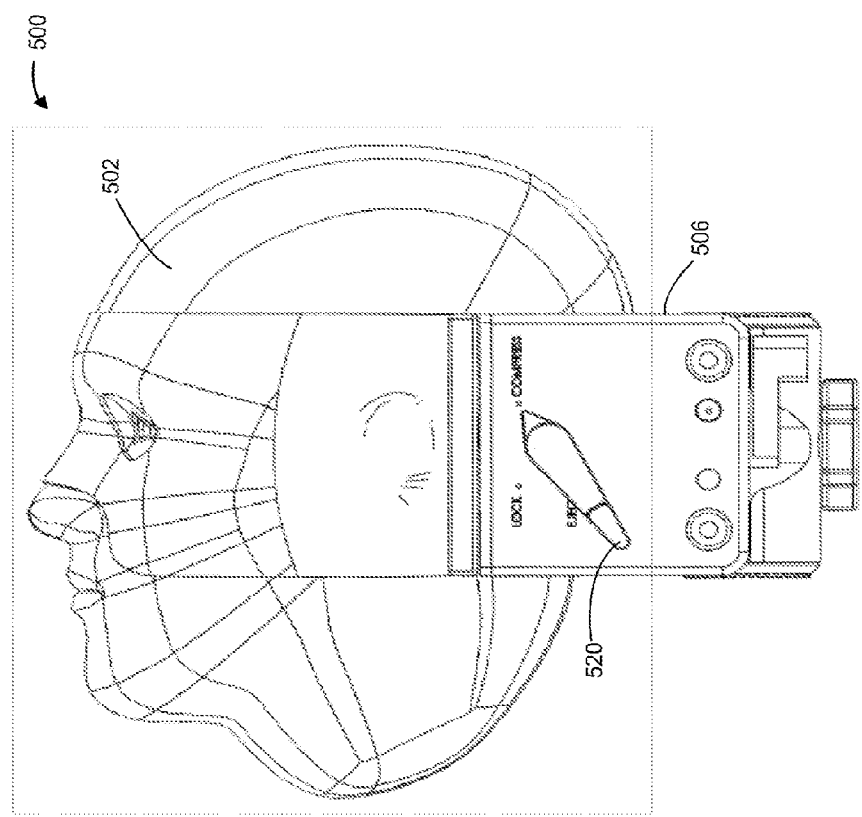

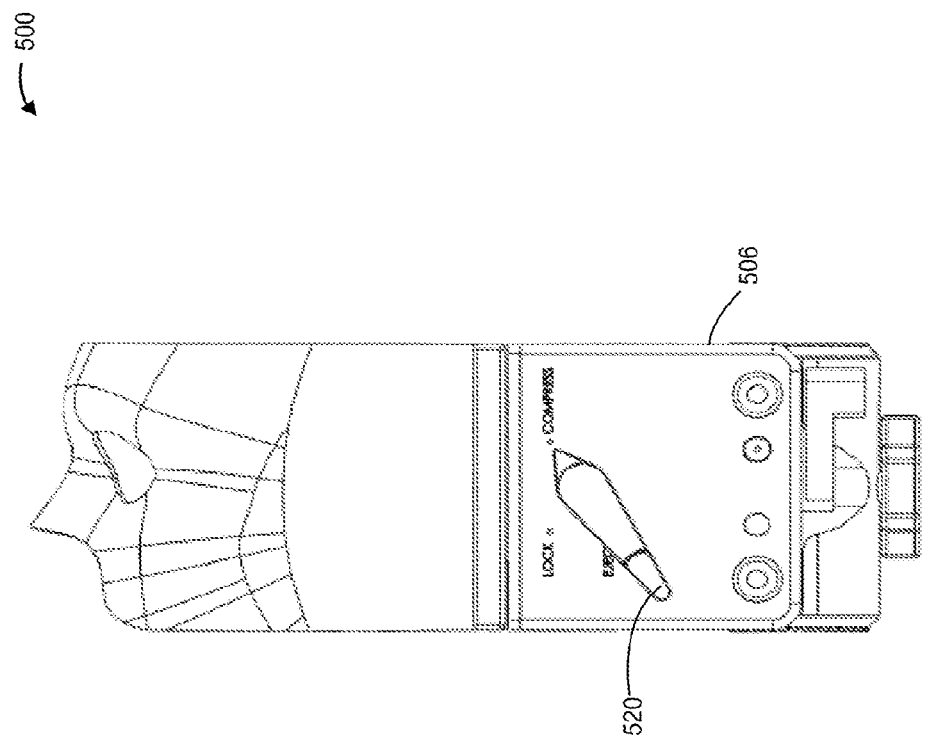

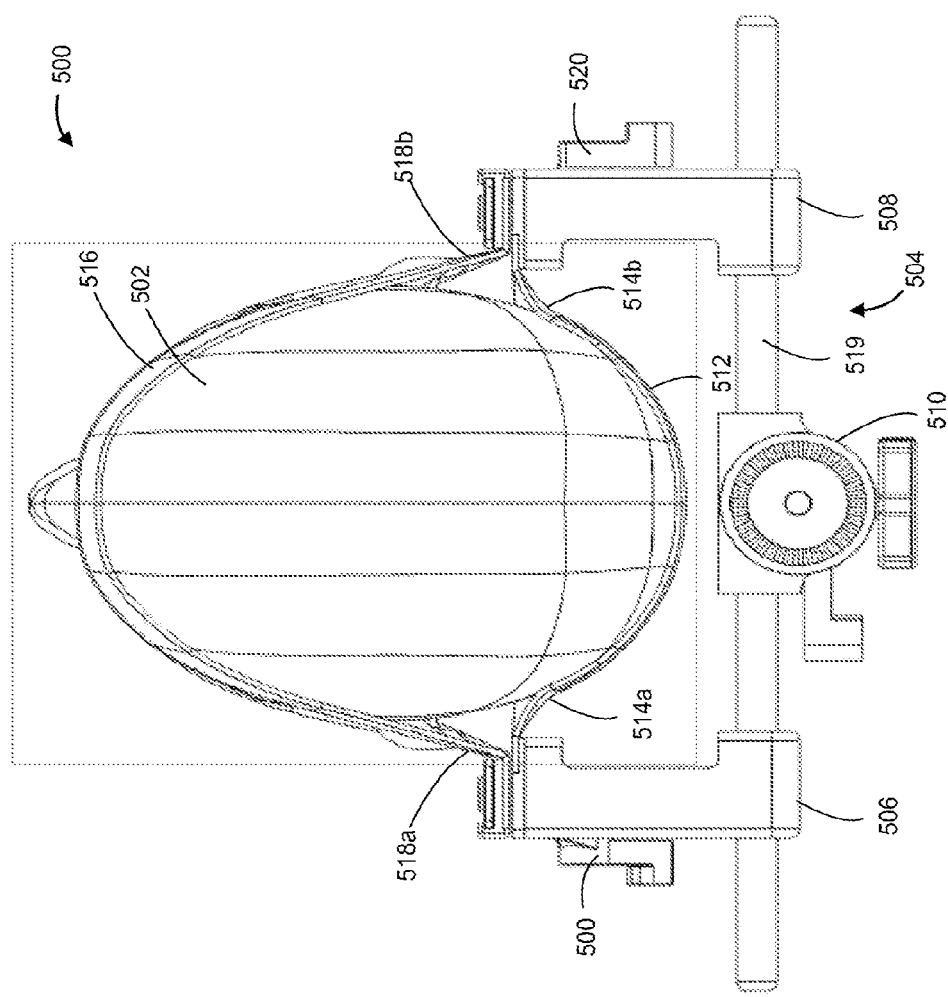

HEAD RESTRAINING APPARATUS FOR A MEDICAL PROCEDURE

TECHNICAL FIELD

The present disclosure is generally related to neurosurgical or medical procedures where head immobilization is needed, and more specifically to a head restraining apparatus for a medical procedure.

BACKGROUND

In a medical procedure, a patient would typically lie on a surgical bed and the patient's head would be restrained in place. Current methods of immobilizing the head typically use pins that are screwed into the skull. The most widely used device is the Mayfield Clamp. Conventional systems for securing a patient's head have shortcomings because the pins may cause damage to the skin and skull.

Further, conventional systems also require the patient to be administered local anesthesia. Once the patient is under anesthesia, it is difficult to gauge overextension and normal range of motion of the neck, which may cause nerve pinching or damage during the procedure. Therefore, there is a need for an improved approach for restraining a patient's head in position during a medical procedure.

SUMMARY

One aspect of the present disclosure provides a head restraining device for securing a patient's head to a bed. The head restraining device comprises a frame, a lower compliant support strap (or band), and an upper compliant support strap (or band). The frame has a first anchor assembly, a second anchor assembly, and a connecting mechanism for connecting the frame to the bed. The lower compliant support strap has a first end and a second end and supports a part of a patient's head in either a supine, prone or decubitus position. The upper compliant support strap having a first end and a second end and secures the remaining part of the patient's face. The first end of the upper compliant support strap and the first end of the lower compliant support strap are securable by the first anchor assembly and the second end of the upper compliant support strap and the second end of the lower compliant support strap are securable by the second anchor assembly.

The lower compliant support strap and the upper compliant support strap may be conformable to contours of the back of the patient's head and the patient's face. The upper and lower compliant support straps may be substantially made of thermoplastic. The thermoplastic may be configured as a mesh and may become compliant when subject to warm water prior to being installed on the patient.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 5A and 5B are perspective views illustrating an exemplary head restraining device for use with the navigation system of FIG. 2 with and without a patient's head, respectively;

FIGS. 6A and 6B are side views illustrating the exemplary head restraining device of FIG. 5 with and without a patient's head, respectively;

FIGS. 7A and 7B are top views illustrating the exemplary head restraining device of FIG. 5 with and without a patient's head, respectively;

DETAILED DESCRIPTION

Figure 1:
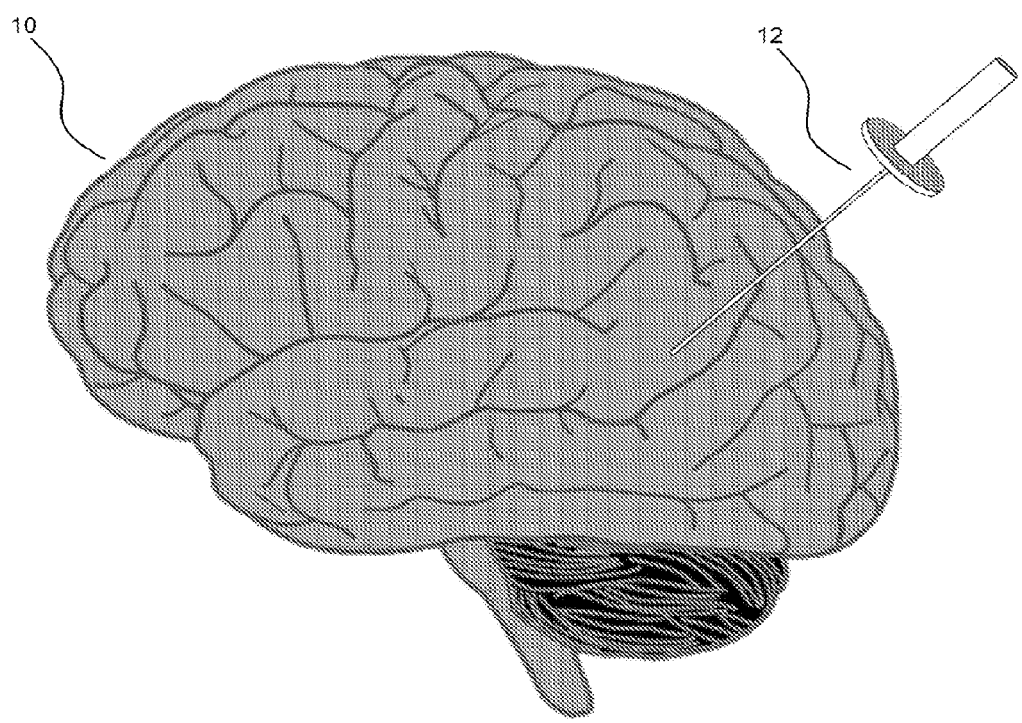
FIG. 1 illustrates the insertion of an access port into a human brain, for providing access to internal brain tissue during a medical procedure.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

Embodiments of the present disclosure provide imaging devices that are insertable into a subject or patient for imaging internal tissues, and methods of use thereof. Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

The present disclosure is generally related to medical procedures, neurosurgery, and minimally invasive port-based surgery in specific.

In the example of a port-based surgery, a surgeon or robotic surgical system may perform a surgical procedure involving tumor resection in which the residual tumor remaining after is minimized, while also minimizing the trauma to the healthy white and grey matter of the brain. In such procedures, trauma may occur, for example, due to contact with the access port, stress to the brain matter, unintentional impact with surgical devices, and/or accidental resection of healthy tissue. A key to minimizing trauma is ensuring that the spatial location of the patient as understood by the surgeon and the surgical system is as accurate as possible.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO Brain Path. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments would then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumour) of the medical procedure. These optical tracking systems require a knowledge of the dimensions of the instrument being tracked so that, for example, the optical tracking system knows the position in space of a tip of a medical instrument relative to the tracking markers being tracked.

Figure 2:
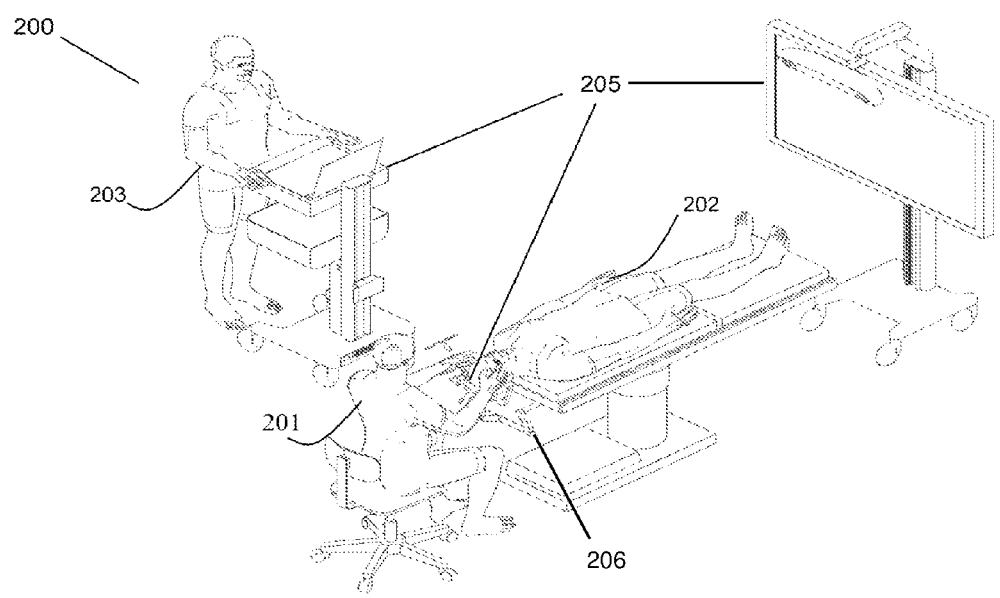
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system, displays and tracked instruments assist the surgeon 201 during his procedure. An operator 203 is also present to operate, control and provide assistance for the medical navigation system 205.

Figure 3:
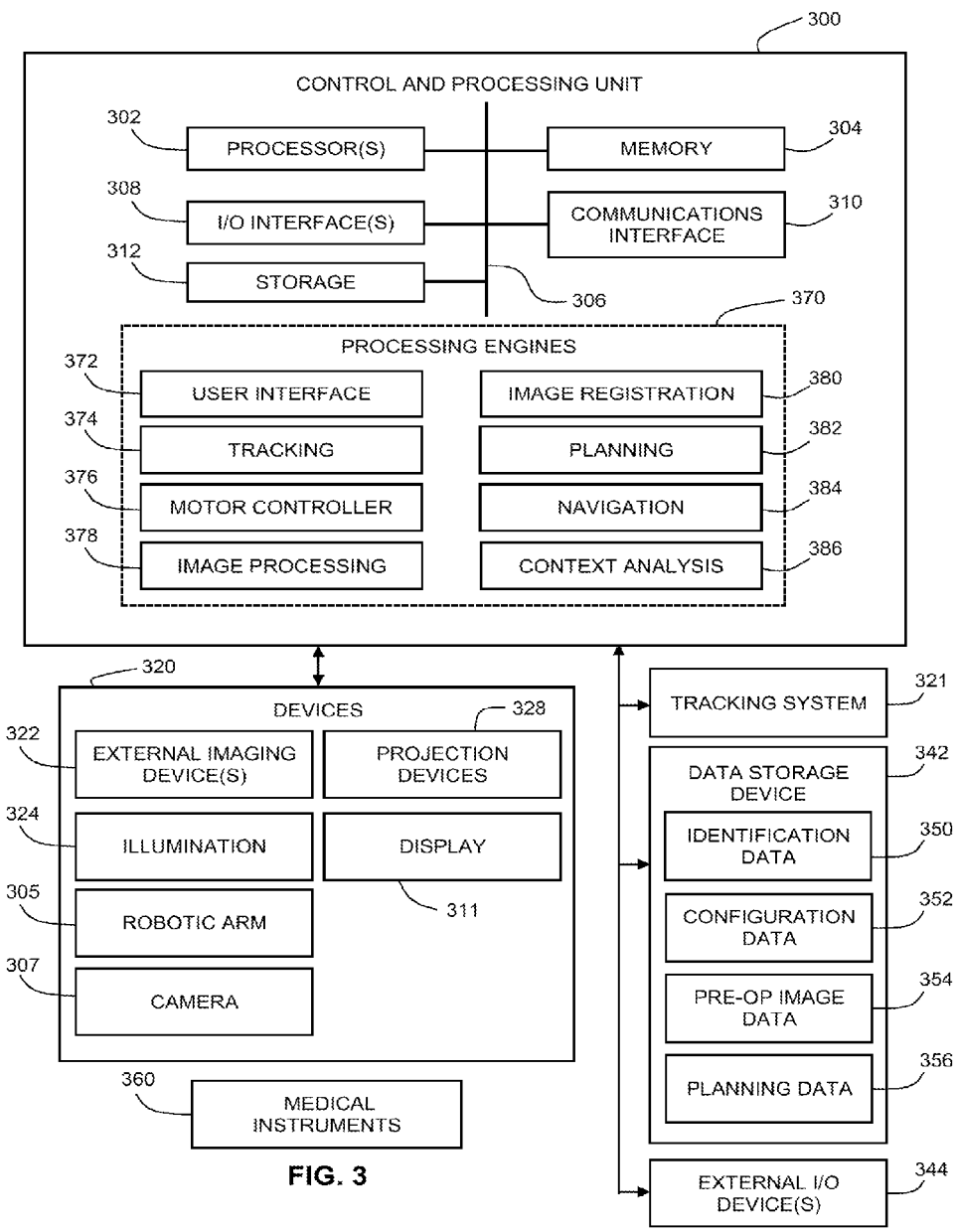
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 3 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, as sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, a robotic arm, one or more projection devices 328, and one or more displays 311.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the neurosurgeon that will lead to the most informed, least damaging neurosurgical operations. In addition to removal of brain tumours and intracranial hemorrhages (ICH), the navigation system 205 can also be applied to a brain biopsy, a functional/deep-brain stimulation, a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using optical tracking instead of infrared cameras.

Figure 4A:
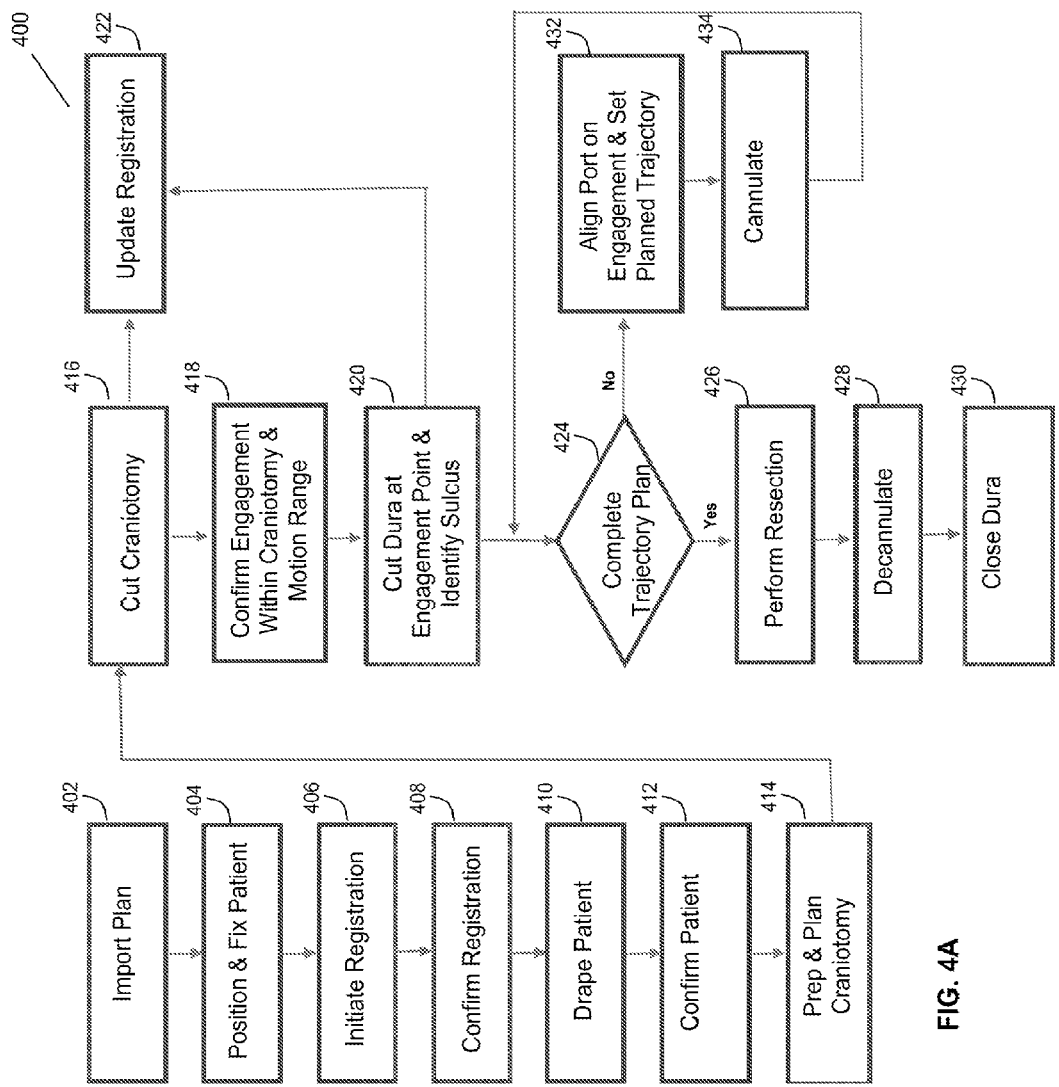
FIG. 4A is a flow chart illustrating a method involved in a surgical procedure using the navigation system of FIG. 2.

Referring to FIG. 4A, a flow chart is shown illustrating a method 400 of performing a port-based surgical procedure using a navigation system, such as the medical navigation system 200 described in relation to FIG. 2. At a first block 402, the port-based surgical plan is imported. A detailed description of the process to create and select a surgical plan is outlined in international publication WO/2014/139024, entitled "PLANNING, NAVIGATION AND SIMULATION SYSTEMS AND METHODS FOR MINIMALLY INVASIVE THERAPY", which claims priority to U.S. Provisional Patent Application Ser. Nos. 61/800,155 and 61/924,993, which are all hereby incorporated by reference in their entirety.

Once the plan has been imported into the navigation system at the block 402, the patient is placed on a surgical bed. The head position is confirmed with the patient plan in the navigation system (block 404), which in one example may be implemented by the computer or controller forming part of the equipment tower 201.

Next, registration of the patient is initiated (block 406). The phrase "registration" or "image registration" refers to the process of transforming different sets of data into one coordinate system. Data may include multiple photographs, data from different sensors, times, depths, or viewpoints. The process of "registration" is used in the present application for medical imaging in which images from different imaging modalities are co-registered. Registration is used in order to be able to compare or integrate the data obtained from these different modalities to the patient in physical space.

Those skilled in the relevant arts will appreciate that there are numerous registration techniques available and one or more of the techniques may be applied to the present example. Non-limiting examples include intensity-based methods that compare intensity patterns in images via correlation metrics, while feature-based methods find correspondence between image features such as points, lines, and contours. Image registration methods may also be classified according to the transformation models they use to relate the target image space to the reference image space. Another classification can be made between single-modality and multi-modality methods. Single-modality methods typically register images in the same modality acquired by the same scanner or sensor type, for example, a series of magnetic resonance (MR) images may be co-registered, while multi-modality registration methods are used to register images acquired by different scanner or sensor types, for example in magnetic resonance imaging (MRI) and positron emission tomography (PET). In the present disclosure, multi-modality registration methods may be used in medical imaging of the head and/or brain as images of a subject are frequently obtained from different scanners. Examples include registration of brain computerized tomography (CT)/MRI images or PET/CT images for tumor localization, registration of contrast-enhanced CT images against non-contrast-enhanced CT images, and registration of ultrasound and CT to patient in physical space.

Figure 4B:
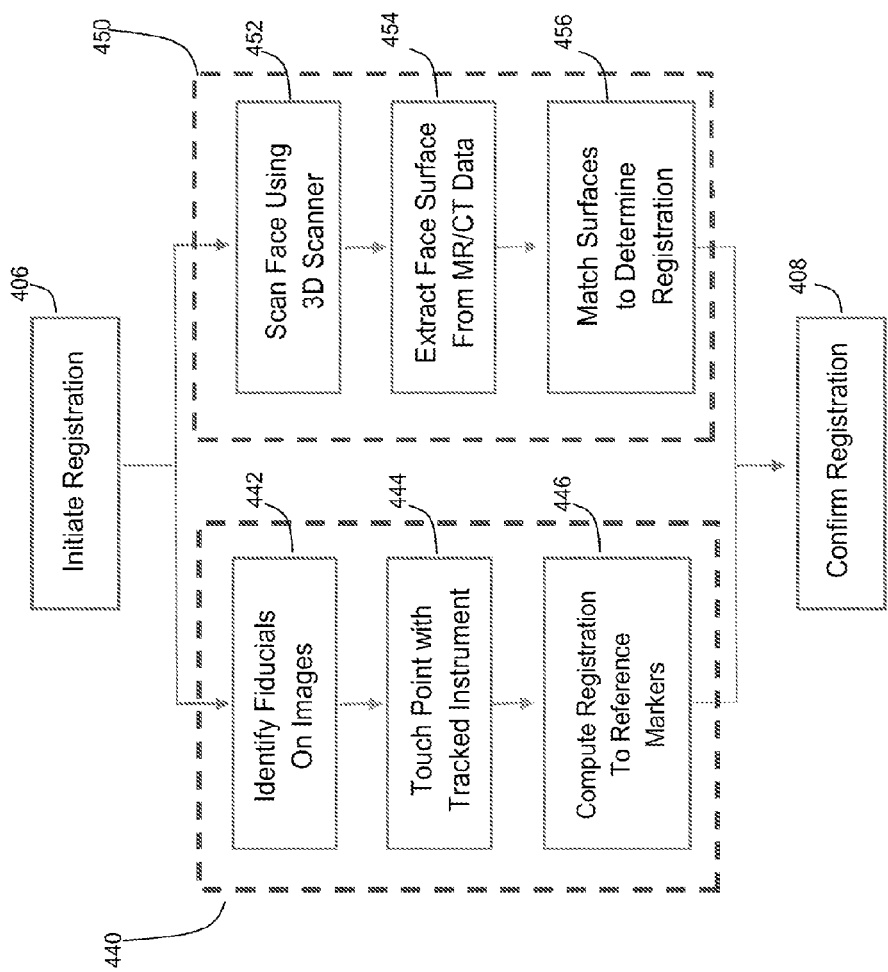
FIG. 4B is a flow chart illustrating a method of registering a patient for a surgical procedure as outlined in FIG. 4A.

Referring now to FIG. 4B, a flow chart is shown illustrating a method involved in registration block 406 as outlined in FIG. 4A, in greater detail. If the use of fiducial touch points (440) is contemplated, the method involves first identifying fiducials on images (block 442), then touching the touch points with a tracked instrument (block 444). Next, the navigation system computes the registration to reference markers (block 446).

Alternately, registration can also be completed by conducting a surface scan procedure (block 450). The block 450 is presented to show an alternative approach, but may not typically be used when using a fiducial pointer. First, the face is scanned using a 3D scanner (block 452). Next, the face surface is extracted from MR/CT data (block 454). Finally, surfaces are matched to determine registration data points (block 456).

Upon completion of either the fiducial touch points (440) or surface scan (450) procedures, the data extracted is computed and used to confirm registration at block 408, shown in FIG. 4A.

Referring back to FIG. 4A, once registration is confirmed (block 408), the patient is draped (block 410). Typically, draping involves covering the patient and surrounding areas with a sterile barrier to create and maintain a sterile field during the surgical procedure. The purpose of draping is to eliminate the passage of microorganisms (e.g., bacteria) between non-sterile and sterile areas. At this point, conventional navigation systems require that the non-sterile patient reference is replaced with a sterile patient reference of identical geometry location and orientation. Numerous mechanical methods may be used to minimize the displacement of the new sterile patient reference relative to the non-sterile one that was used for registration but it is inevitable that some error will exist. This error directly translates into registration error between the surgical field and pre-surgical images. In fact, the further away points of interest are from the patient reference, the worse the error will be.

Upon completion of draping (block 410), the patient engagement points are confirmed (block 412) and then the craniotomy is prepared and planned (block 414).

Upon completion of the preparation and planning of the craniotomy (block 414), the craniotomy is cut and a bone flap is temporarily removed from the skull to access the brain (block 416). Registration data is updated with the navigation system at this point (block 422).

Next, the engagement within craniotomy and the motion range are confirmed (block 418). Next, the procedure advances to cutting the dura at the engagement points and identifying the sulcus (block 420).

Thereafter, the cannulation process is initiated (block 424). Cannulation involves inserting a port into the brain, typically along a sulci path as identified at 420, along a trajectory plan. Cannulation is typically an iterative process that involves repeating the steps of aligning the port on engagement and setting the planned trajectory (block 432) and then cannulating to the target depth (block 434) until the complete trajectory plan is executed (block 424).

Once cannulation is complete, the surgeon then performs resection (block 426) to remove part of the brain and/or tumor of interest. The surgeon then decannulates (block 428) by removing the port and any tracking instruments from the brain. Finally, the surgeon closes the dura and completes the craniotomy (block 430). Some aspects of FIG. 4A are specific to port-based surgery, such as portions of blocks 428, 420, and 434, but the appropriate portions of these blocks may be skipped or suitably modified when performing non-port based surgery.

When performing a surgical procedure using a medical navigation system 205, as outlined in connection with FIGS. 4A and 4B, the medical navigation system 205 must acquire and maintain a reference of the location of the tools in use as well as the patient in three dimensional (3D) space. In other words, during a navigated neurosurgery, there needs to be a tracked reference frame that is fixed relative to the patient's skull. During the registration phase of a navigated neurosurgery (e.g., the step 406 shown in FIGS. 4A and 4B), a transformation is calculated that maps the frame of reference of preoperative MRI or CT imagery to the physical space of the surgery, specifically the patient's head. This may be accomplished by the navigation system 205 tracking locations of fiducial markers fixed to the patient's head, relative to the static patient reference frame. The patient reference frame is typically rigidly attached to the head fixation device, such as a Mayfield clamp or may be attached to the device described below in connection with FIGS. 5-11. Registration is typically performed before the sterile field has been established (e.g., the step 410 shown in FIG. 4A).

Conventional methods of immobilizing the head of a patient for surgery typically use pins that are screwed into the skull. The most widely used device for this purpose is the Mayfield Clamp. It would be desirable to achieve head immobilization without the use of pins, since pins tend to cause damage to skin and the skull and require local anesthesia. Skin movement can make it difficult to achieve complete or nearly complete fixation of the head so that the patient can be used with the medical navigation system 205. Further, once the patient is under anesthesia, it is difficult to gage overextension and normal range of motion of the neck, which may cause nerve pinching or damage during the medical procedure. By designing a head holding device with a "known" range of motion predetermined to be safe, the medical procedure can be conducted with less risk of harm to the patient.

Aspects of the present disclosure may be applied to surgical or medical procedures where head immobilization is required. Aspects of the present disclosure may enable head movement in the normal range of motion (e.g., up to 60° flexion, up to 50° extension, up to 45° lateral flexion, up to 80° rotation) and the head of the patient may be fixed at any angle within such range of motion.

Aspects of the present disclosure may provide an articulating frame and/or thermoplastic mesh or an articulating tabletop and/or a thermoplastic mesh, which may allow for intraoperative magnetic resonance (MR) imaging and may be compatible with navigation systems such as the medical navigation system 205.

Figure 5A:
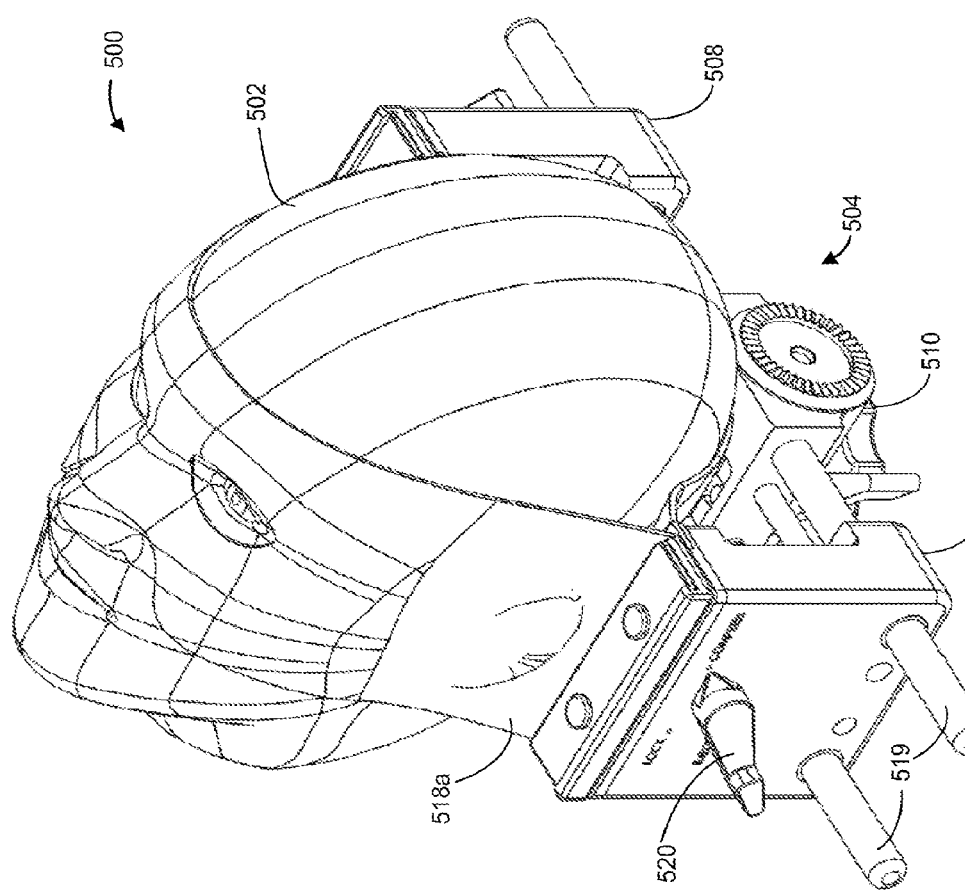
Figure 7B:
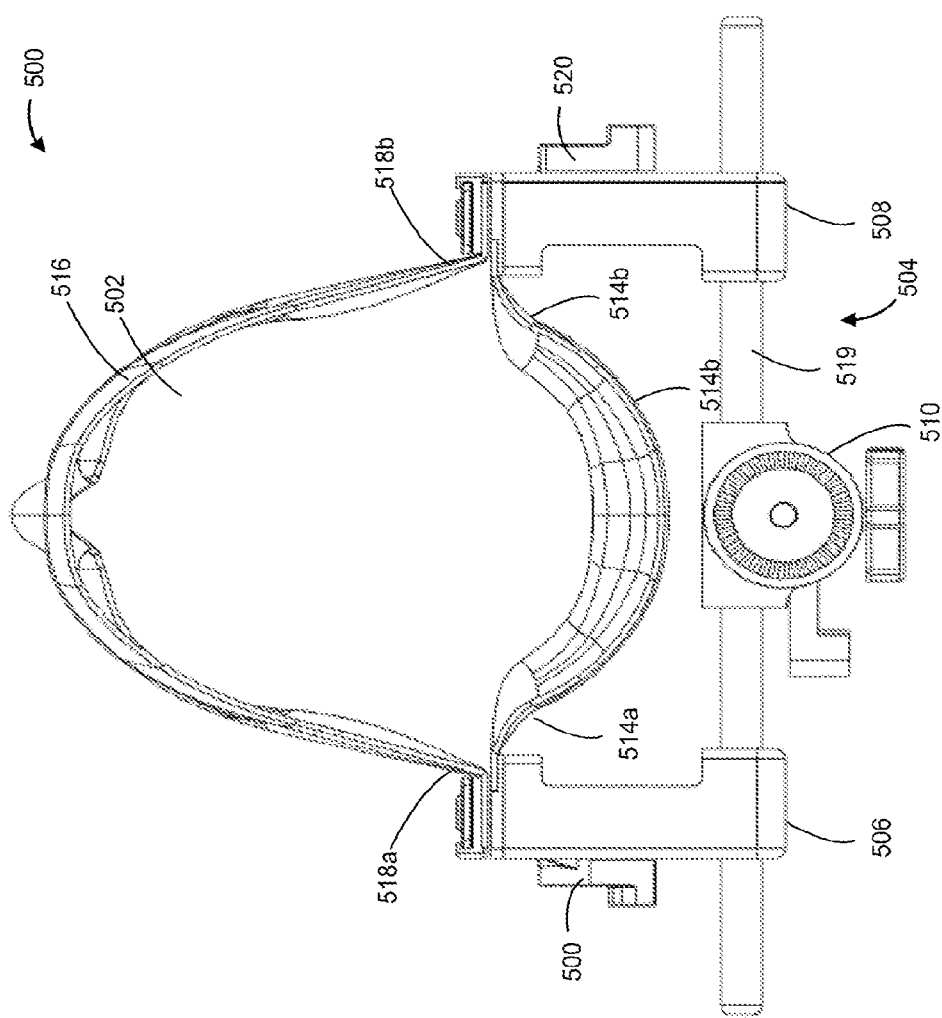
Figure 8A:
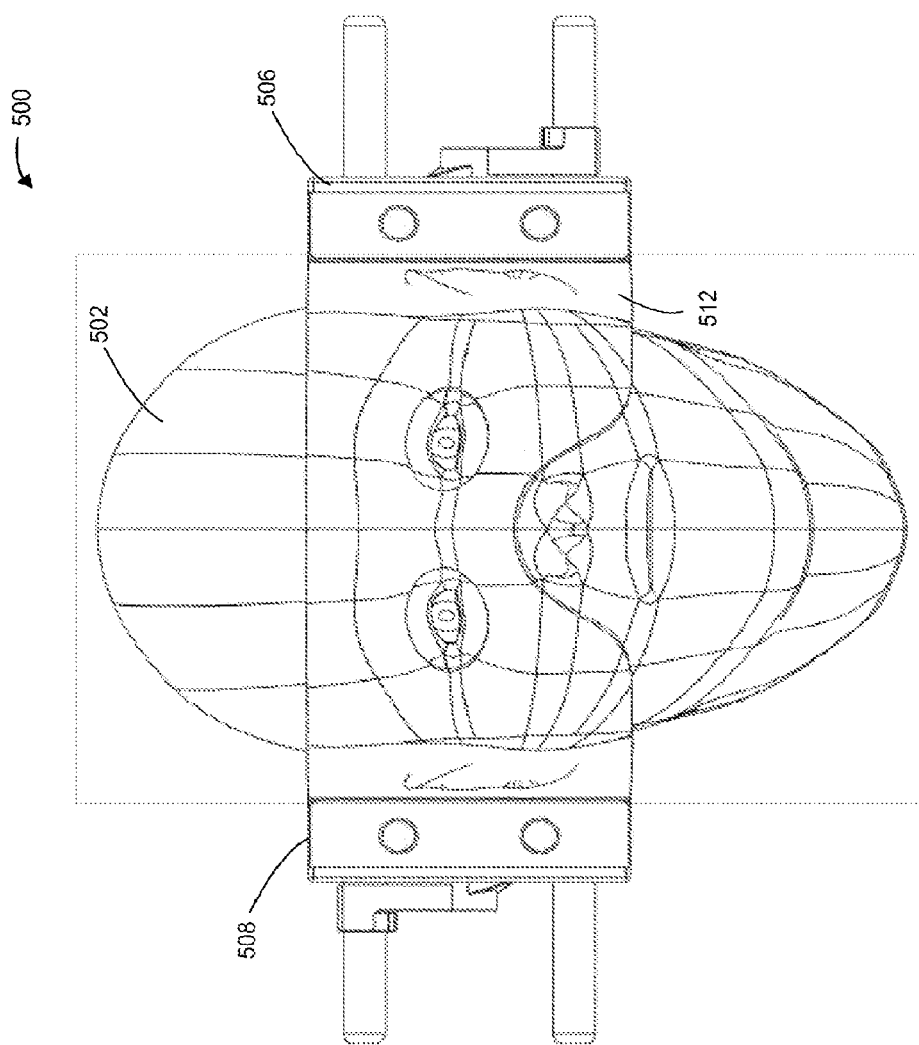
FIGS. 8A and 8B are front views illustrating the exemplary head restraining device of FIG. 5 with and without a patient's head, respectively.
Figure 8B:
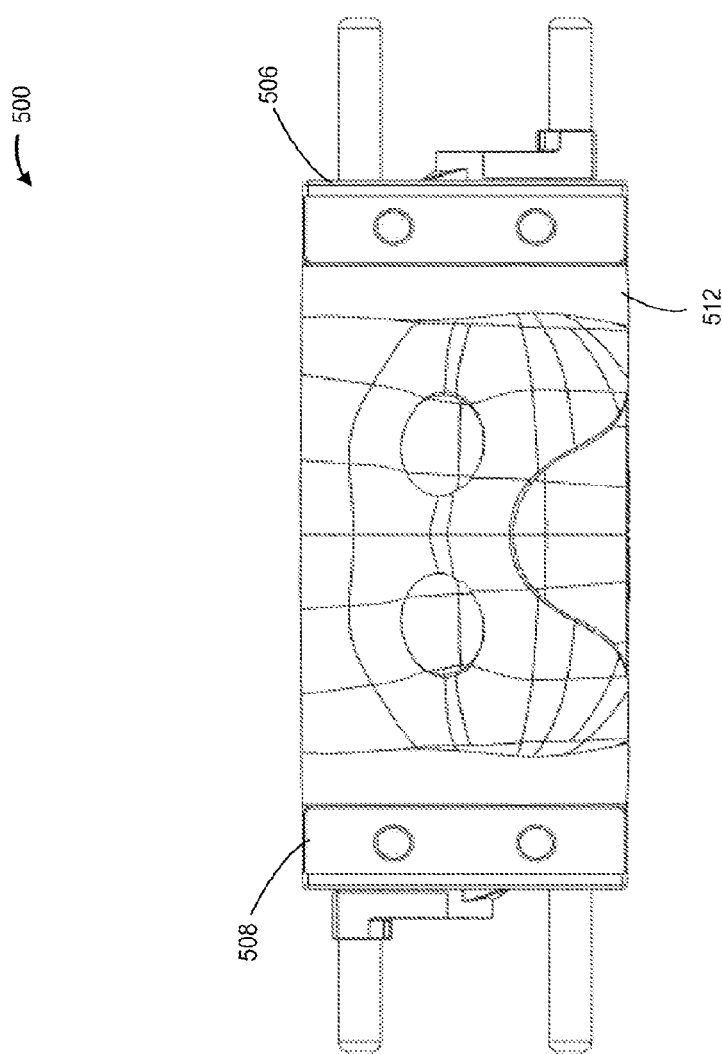
Figure 9A:
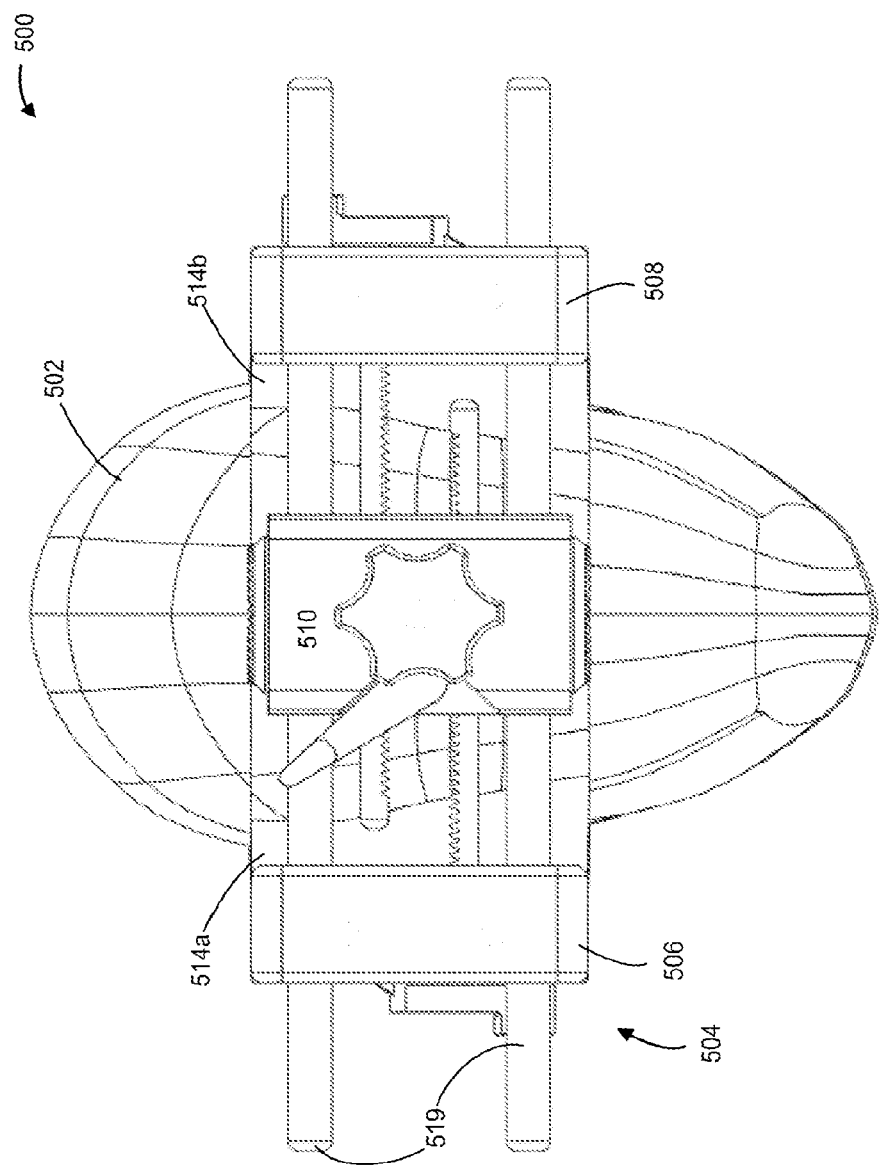
FIGS. 9A and 9B are bottom side views illustrating the exemplary head restraining device of FIG. 5 with and without a patient's head, respectively.
Figure 9B:
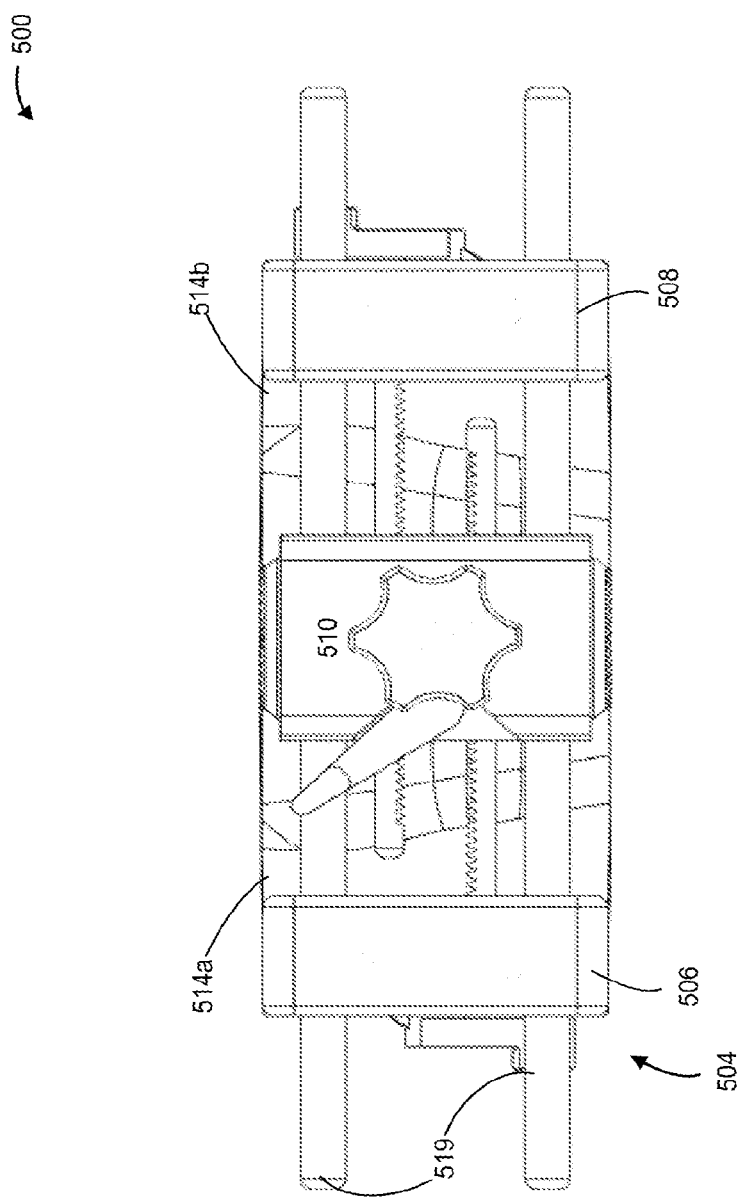
Figure 10:
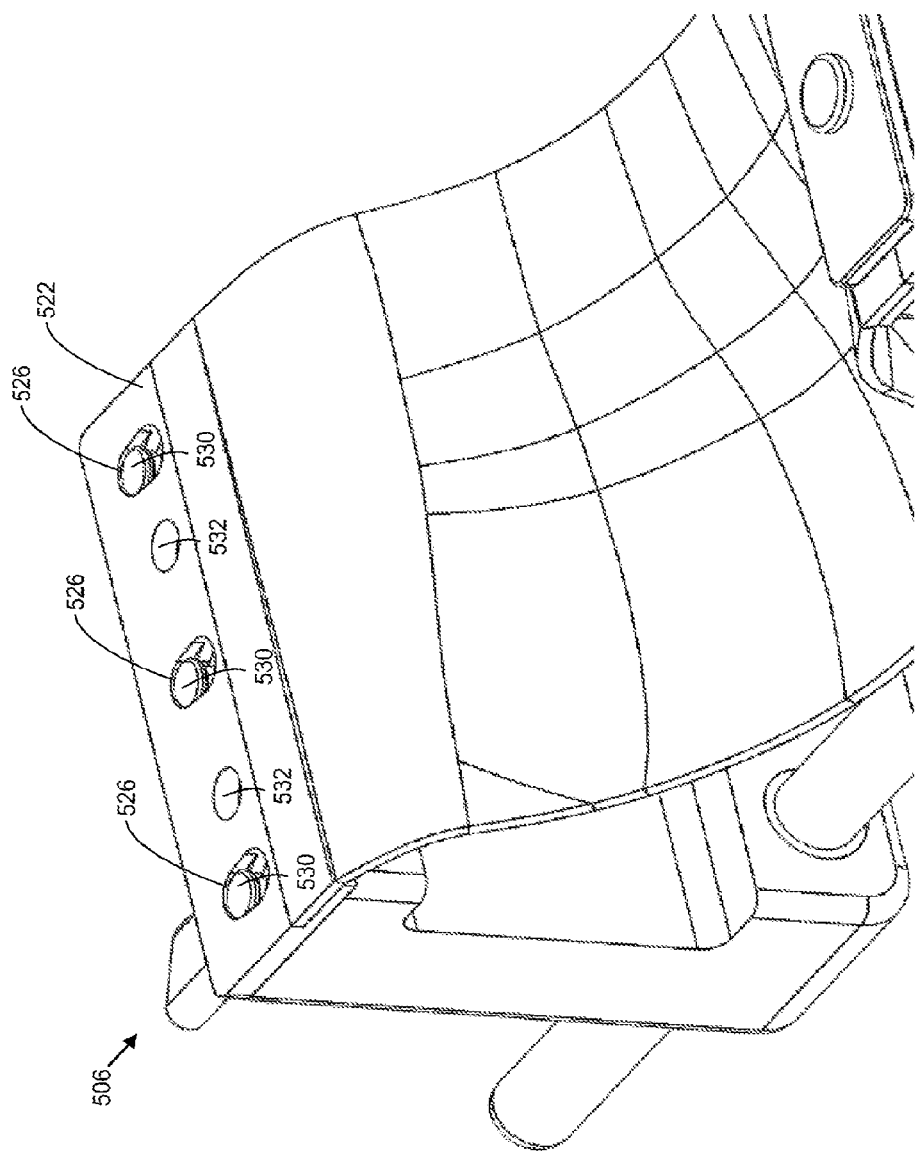
FIG. 10 is a perspective view illustrating an exemplary anchor assembly of the exemplary head restraining device of FIG. 5.
Figure 11:
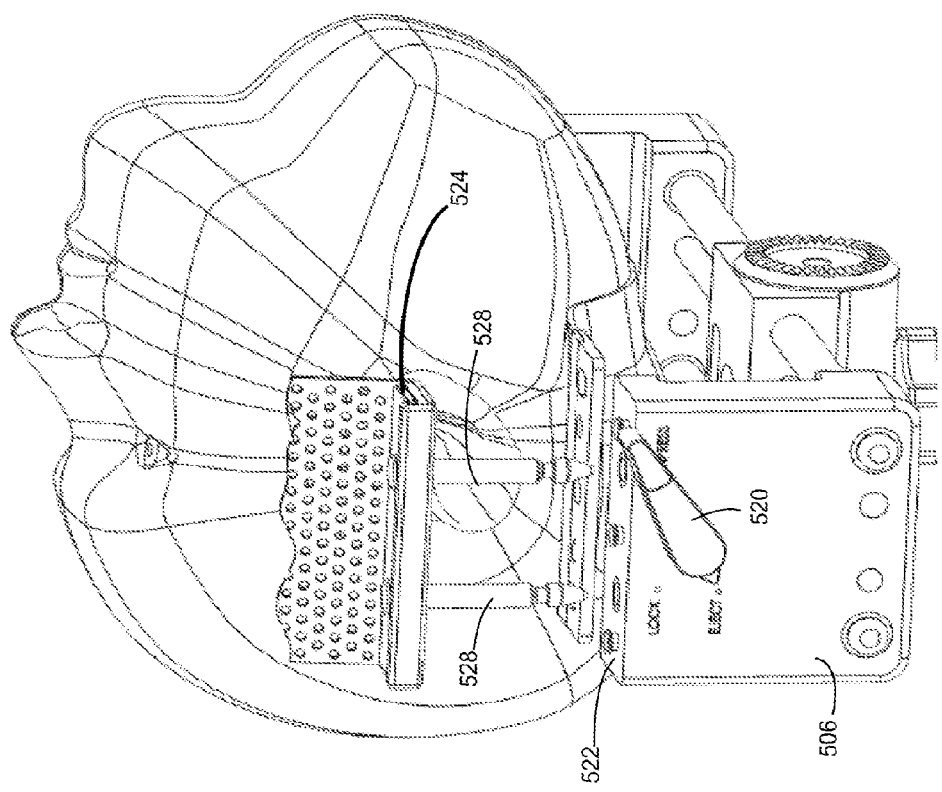
FIG. 11 is a side view and partially exploded view of the exemplary anchor assembly shown in FIG. 10.

Referring to FIGS. 5A and 5B, perspective drawings are shown illustrating an exemplary head restraining device 500 for use with the navigation system of FIG. 2 with and without a patient's head, respectively. FIGS. 6A and 6B are side views illustrating the exemplary head restraining device 500 of FIG. 5 with and without a patient's head, respectively. FIGS. 7A and 7B are top views illustrating the exemplary head restraining device 500 of FIG. 5 with and without a patient's head, respectively. FIGS. 8A and 8B are front views illustrating the exemplary head restraining device 500 of FIG. 5 with and without a patient's head, respectively. FIGS. 9A and 9B are bottom views illustrating the exemplary head restraining 500 device of FIG. 5 with and without a patient's head, respectively. FIG. 10 is a perspective view illustrating an exemplary anchor assembly of the exemplary head restraining device 500 of FIG. 5. FIG. 11 is a side view and partially exploded view of the exemplary anchor assembly shown in FIG. 10. FIGS. 5-11 will now be discussed concurrently.

Head restraining device 500 aims to secure a patient's head 502 to a bed, such as a hospital bed, table top, moveable table top, stretcher, Gurney, or any other suitable surface on which medical treatment may be administered. In one example, the head restraining device 500 may be configured to sufficiently restrain the patient's head 502 to accommodate surgery or treatment. The head restraining device 500 may be trackable by surgical navigation systems, eliminating the need for an external patient reference marker.

In the examples presented herein, the head restraining device 500 is described as being attached to a bed, but is not limited to being attached to a bed and may be attached to any suitable surface for performing a medical procedure. The head restraining device 500 has a frame 504 having a first anchor assembly 506, a second anchor assembly 508, and a connecting mechanism 510 for connecting the frame to the bed.

The head restraining device 502 as seen in FIG. 5, has a lower support strap 512 having a first end 514a and a second end 514b. The lower support strap 512 may function as supporting at least part of a patient's head. The head restraining device 502 has an upper support strap 516 having a first end 518a and a second end 518b. The upper support strap 516 may function to secure at least part of the patient's face. In alternate embodiments, the support straps 512, 516 of head restraining device 502 may be configured to support the patient in any orientation (e.g. supine, prone or decubitus position).

The upper support strap 516 and the lower support strap 512 may be referred to as compliant support straps, meaning that the support straps 512, 516 may be conformable to contours of the patient's head. In other words, the compliant support straps 512, 516 may adjust and adhere to the shape of the back of the patient's head, the patient's face, and the patient's sides of the head. The upper and lower compliant support straps 516, 512 may be made of any suitable material such as from an airbag, a foam material, a moldable pillow, or a mesh material. In one example, the upper and lower compliant support straps 516, 512 may be substantially made of thermoplastic. In one example, the thermoplastic may be configured as a mesh and may become compliant when subject to heat such as by using warm water prior to installing the support straps 516, 512 on the patient. The thermoplastic may be quickly dried, put into place and tightened to conform to the patient's head, with the thermoplastic quickly adapting the form of the patient's head 502 and maintaining that form as the thermoplastic cools. While a specific example of thermoplastic has been provided as an example of a suitable material for the compliant support straps 512, 516, any suitable material may be used according to the design criteria of a particular application. Further, the thermoplastic need not be in a mesh configuration, but may be in any suitable configuration.

In one example, the first end 518a of the upper compliant support strap 516 and the first end 514a of the lower compliant support strap 512 are securable by the first anchor assembly 506 and the second end 518b of the upper compliant support strap 516 and the second end 514b of the lower compliant support strap 512 are securable by the second anchor assembly 508.

In one example, the first anchor assembly 506 and the second anchor assembly 508 are laterally slideable on one or more sliding members 519 of the frame 504 for adjustment to a width of the patient's head 502. While FIGS. 5, 7, 8, and 9 show two sliding members 519, any number of sliding members 519 may be used to meet the design criteria of a particular application. In one example, the sliding members 519 of the frame 504 may be mountable on a hospital bed, for example using the connecting mechanism 510.

In one example, the first anchor assembly 506 and the second anchor assembly 508 has a locking mechanism 520 that provides for: (a) releasing at least one of the upper and lower compliant support straps 516, 512 in an unlocked mode; (b) a lock feature for locking position of at least one of the upper and lower compliant support straps 516, 512 in a locked mode, and (c) a compression feature for tightening at least one of the upper and lower compliant support straps 516, 512 in a compressed mode. Locking mechanism 520 may be a switch, button, lever or knob, or any other suitable control mechanism. The locking mechanism 520 is not restricted to the locking mechanism 520, but may include any other mechanism that allows for the described type of locking, unlocking, and compression ability (e.g., springs, hyrdraulics, pneumatics, electrical control, pistons, etc).

In another example, a first type of anchor plate 522 (FIGS. 10 and 11) is attached to each of the first end 514a of the lower compliant support strap 512 and the second end 514b of the lower compliant support strap 512. A second type of anchor plate 524 (FIG. 11) is attached to each of the first end 518a of the upper compliant support strap 516 and the second end 518b of the upper compliant support strap 516. In one example, the first type of anchor plate 522 includes a plate having mounting holes 526 and mounting holes 532 formed therein and the second type of anchor plate 524 includes a plate having mounting features 528 attached thereto. Mounting features 528 may include dowels. Anchor plates 522 and 524, may be made of any suitable material according to the design criteria of a particular application. Examples of anchor plate material may include metal, plastic, wood, or synthetic materials of suitable strength. In an example embodiment, anchor plates 522 and 524 may be MRI compatible and sterilizable.

In one example, the first anchor plate 522 of the first end 514a of the lower compliant support strap 512 fits over mounting pins 530 of the first anchor assembly 506 and the first anchor plate 522 of the second end 514b of the lower compliant support strap 512 fits over mounting pins 530 of the second anchor assembly 508. The mounting features 528 of the second anchor plate 524 of the first end 518a of the upper compliant support strap 516 fit through mounting features 532 of the first anchor plate 522 of the first end 514a of the lower compliant support strap 512 and into mounting features of the first anchor assembly 506 and the mounting features 528 of second anchor plate 524 of the second end 518b of the upper compliant support strap 516 fit through the mounting features 532 of the first anchor plate 522 of the second end 514b of the lower compliant support strap 512 and into mounting features of the second anchor assembly 508. This procedure may be quickly executed after the compliant support straps 512, 516 have been warmed in warm water and dried and placed in position under and over the patient's head. The locking mechanism 520 may then moved to the compress position where the support straps 512, 516 are rendered tight, for example by the first anchor assembly 506 and the second anchor assembly 508 moving away from each other by sliding on the sliding members 519. The locking mechanism 520 may then be moved to the lock position, where the tightness of the support straps 512, 516 is maintained.

The first end 518a of the upper compliant support strap 516 and the first end 514a of the lower compliant support strap 512 may be securable by the first anchor assembly 506 adjacent to a first ear of the patient. Likewise, the second end 518b of the upper compliant support strap 516 and the second end 514b of the lower compliant support strap 512 may be securable by the second anchor assembly 508 adjacent to a second ear of the patient. While this configuration is provided as an example, any suitable position of the first anchor assembly 506 and the second anchor assembly 508 may be used to have the upper and lower compliant support straps 512, 516 meet anywhere around the periphery of the patient's head.

In one example, the upper compliant support strap 516 may include a plurality of upper compliant support straps (e.g., two or more) and the lower compliant support strap 512 may include a plurality of lower compliant support straps (e.g., two or more). In another example, the upper compliant support strap 516 and the lower compliant support strap 512 may each have widths that are substantially equal. In yet another example, the upper compliant support strap 516 and the lower compliant support strap 512 may each have widths that are not substantially equal and one support strap may be substantially wider than the other. In another example, the upper compliant support strap 516 may have a width that runs substantially from the patient's mouth to the patient's forehead. In another example, the upper compliant support strap 516 and/or the lower compliant support strap 512 may have a width that substantially covers the patient's entire face or head.

The upper compliant support strap 516 may have at least one cutout that may include one or more cutouts for the patient's eyes and/or a cutout for the patient's nose, and/or a cutout for the patient's mouth.

In one example, the head restraining device 500 provides for head position movement in a normal range of motion including up to substantially 60° flexion, up to substantially 50° extension, up to substantially 45° lateral flexion, and up to substantially 80° rotation with the head position being lockable at any angle within the normal range of motion. The head position movement may be provided by a suitable arm 206 that connects to the connecting mechanism 510.

In one example, steriled drape that covers the lower portion of the patient as well as equipment that is not sterilized is attachable to the upper and lower compliant support straps 516, 512. Tracking markers for use with the navigation system 205 may also be attached to one or both of the upper and lower compliant support straps 516, 512. In another example, the access port 12 may be attached to one or both of the upper and lower compliant support straps 516, 512 instead of the conventional approach of using a Sheppard's Hook.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

I claim:

1. A head restraining device for securing a patient's head to a bed, the head restraining device comprising:
   a frame having a first anchor assembly, a second anchor assembly, and a connecting mechanism for connecting the frame to the bed;
   a lower compliant support strap having a first end and a second end, the lower compliant support strap for supporting at least part of a patient's head; and an upper compliant support strap having a first end and a second end, the upper compliant support strap for securing at least part of the patient's head;
   wherein the first end of the upper compliant support strap and the first end of the lower compliant support strap are securable by the first anchor assembly and the second end of the upper compliant support strap and the second end of the lower compliant support strap are securable by the second anchor assembly, and wherein the lower compliant support strap and the upper compliant support strap are conformable to contours of the patient's head,
   wherein an arm connected to the connecting mechanism of the head restraining device allows for head positioning movement in a normal range of motion including up to substantially 60° flexion, up to substantially 50° extension, up to substantially 45° lateral flexion, and up to substantially 80° rotation with a head position being lockable at any angle within the normal range of motion.

2. The head restraining device according to claim 1, further comprising:
   a first anchor plate attached to each of the first end of the lower compliant support strap and the second end of the lower compliant support strap; and
   a second anchor plate attached to each of the first end of the upper compliant support strap and the second end of the upper compliant support strap.

3. The head restraining device according to claim 2, wherein the first anchor plate includes a plate having mounting holes formed therein and the second anchor plate includes a plate having mounting features attached thereto.

4. The head restraining device according to claim 3, wherein the first anchor plate of the first end of the lower compliant support strap fits over mounting pins of the first anchor assembly and the first anchor plate of the second end of the lower compliant support strap fits over mounting pins of the second anchor assembly and the mounting features of the second anchor plate of the first end of the upper compliant support strap fit through the mounting holes of the first anchor plate of the first end of the lower compliant support strap and into mounting holes of the first anchor assembly and the mounting features of second anchor plate of the second end of the upper compliant support strap fit through the mounting holes of the first anchor plate of the second end of the lower compliant support strap and into mounting holes of the second anchor assembly.

5. The head restraining device according to claim 1 wherein the upper and lower compliant support straps are substantially made of at least one of a thermoplastic material and a conformable material.

6. The head restraining device according to claim 5, wherein the thermoplastic material is configured as a mesh and becomes compliant when subject to warm water prior to being installed on the patient.

7. The head restraining device according to claim 1 wherein the upper compliant support strap has at least one cut out.

8. The head restraining device according to claim 7, wherein the at least one cut out includes a cut out for the patient's eyes and a cut out for the patient's mouth.

9. The head restraining device according to claim 1, wherein the upper and lower compliant support straps are selected from the group consisting of an airbag, an air pouch, a foam material, a moldable pillow, a moldable strap, and a mesh material.

10. The head restraining device according to claim 1, wherein the first anchor assembly and the second anchor assembly are laterally slideable on a sliding member of the frame for adjustment to a width of the patient's head, the sliding member being mountable on a hospital bed with the connecting mechanism.

11. The head restraining device according to claim 1, wherein the head restraining device is configured to restrain the head to accommodate surgery.

12. The head restraining device according claim 1, wherein the first anchor assembly and the second anchor assembly have a release feature for releasing at least one of the upper and lower compliant support straps, a lock feature for locking position of at least one of the upper and lower compliant support straps, and a compression feature for tightening at least one of the upper and lower compliant support straps.

13. The head restraining device according to claim 1, wherein the upper compliant support strap has a width that is configured to run substantially from the patient's mouth to the patient's forehead.

* * * * *